(12) United States Patent
Morgenbesser et al.

(10) Patent No.: US 10,183,422 B2
(45) Date of Patent: Jan. 22, 2019

(54) METHOD FOR PRODUCING A FOIL OR A FILM

(71) Applicant: Berndorf Band GmbH, Berndorf (AT)

(72) Inventors: Karl Morgenbesser, Aspang (AT); Hannes Flasch, Ebreichsdorf (AT); Michael Proschek, Schoenau (AT)

(73) Assignee: Berndorf Band GmbH, Berndorf (AT)

(*) Notice: Subject to any disclaimer, the term of this patent is extended or adjusted under 35 U.S.C. 154(b) by 325 days.

(21) Appl. No.: 14/782,480

(22) PCT Filed: May 14, 2014

(86) PCT No.: PCT/AT2014/050117
§ 371 (c)(1),
(2) Date: Oct. 5, 2015

(87) PCT Pub. No.: WO2014/183145
PCT Pub. Date: Nov. 20, 2014

(65) Prior Publication Data
US 2016/0257038 A1    Sep. 8, 2016

(30) Foreign Application Priority Data
May 15, 2013 (AT) .............................. A 50326/2013

(51) Int. Cl.
*B29C 41/28*    (2006.01)
*B29C 35/02*    (2006.01)
(Continued)

(52) U.S. Cl.
CPC .......... *B29C 41/28* (2013.01); *B29C 35/0288* (2013.01); *B29C 41/44* (2013.01); *B29C 41/46* (2013.01); *B29C 41/52* (2013.01); *G01N 21/86* (2013.01); *B29C 35/0277* (2013.01); *B29K 2105/0073* (2013.01); *B29L 2007/00* (2013.01);
(Continued)

(58) Field of Classification Search
CPC ....................................................... B29C 41/28
See application file for complete search history.

(56) References Cited

U.S. PATENT DOCUMENTS

| 4,582,520 A | 4/1986 | Sturm |
| 4,982,500 A | 1/1991 | Ramani |

(Continued)

FOREIGN PATENT DOCUMENTS

| DE | 24 38 869 A1 | 3/1975 |
| DE | 198 20 948 C1 | 9/1999 |

(Continued)

OTHER PUBLICATIONS

International Search Report of PCT/AT2014/050117, dated Sep. 8, 2014.

*Primary Examiner* — Larry W Thrower
(74) *Attorney, Agent, or Firm* — Collard & Roe, P.C.

(57) ABSTRACT

The invention relates to a method for producing a foil or a film (1), comprising the following steps
a) applying at least one material (2) for producing the foil or the film (1) to a moving belt (3),
b) at least partially curing and/or partially drying the poured material (2), during which step b) the properties of the material and/or thermal state variables of a defined area around the belt (3) are recorded by means of at least one non-invasive spectroscopic method.

7 Claims, 2 Drawing Sheets

(51) Int. Cl.
  *B29C 41/46* (2006.01)
  *B29C 41/52* (2006.01)
  *G01N 21/86* (2006.01)
  *B29C 41/44* (2006.01)
  *B29K 105/00* (2006.01)
  *G01N 21/84* (2006.01)
  *G01N 21/35* (2014.01)
  *B29L 7/00* (2006.01)

(52) U.S. Cl.
  CPC . *G01N 21/8422* (2013.01); *G01N 2021/3595* (2013.01); *G01N 2021/8416* (2013.01)

(56) References Cited

U.S. PATENT DOCUMENTS

| | | |
|---|---|---|
| 2004/0058179 A1 | 3/2004 | Yamazaki et al. |
| 2007/0075870 A1 | 4/2007 | McCauley et al. |
| 2010/0284603 A1 | 11/2010 | Howe |
| 2011/0111130 A1 | 5/2011 | Hickl et al. |
| 2012/0292800 A1* | 11/2012 | Higuchi ............... B29C 41/28 264/40.1 |

FOREIGN PATENT DOCUMENTS

| | | |
|---|---|---|
| DE | 10 2010 021260 A1 | 11/2011 |
| DE | 10 2011 008 188 A1 | 7/2012 |
| EP | 1 134 063 A1 | 9/2001 |
| EP | 1 180 660 A2 | 2/2002 |
| GB | 1 483 215 A | 8/1977 |
| JP | S61-219625 A | 9/1986 |
| JP | S62-219625 A | 9/1987 |
| JP | 2004-111761 A | 4/2004 |
| JP | 2006-265405 A | 10/2006 |
| JP | 2008-157634 A | 7/2008 |
| JP | 2011-208011 A | 10/2011 |
| JP | 2011-246307 A | 12/2011 |
| TW | 201002438 A | 1/2010 |
| TW | 201134656 A1 | 10/2011 |
| WO | 84/01430 A | 4/1984 |
| WO | 89/09388 A1 | 10/1989 |
| WO | 20061101251 A1 | 9/2006 |

* cited by examiner

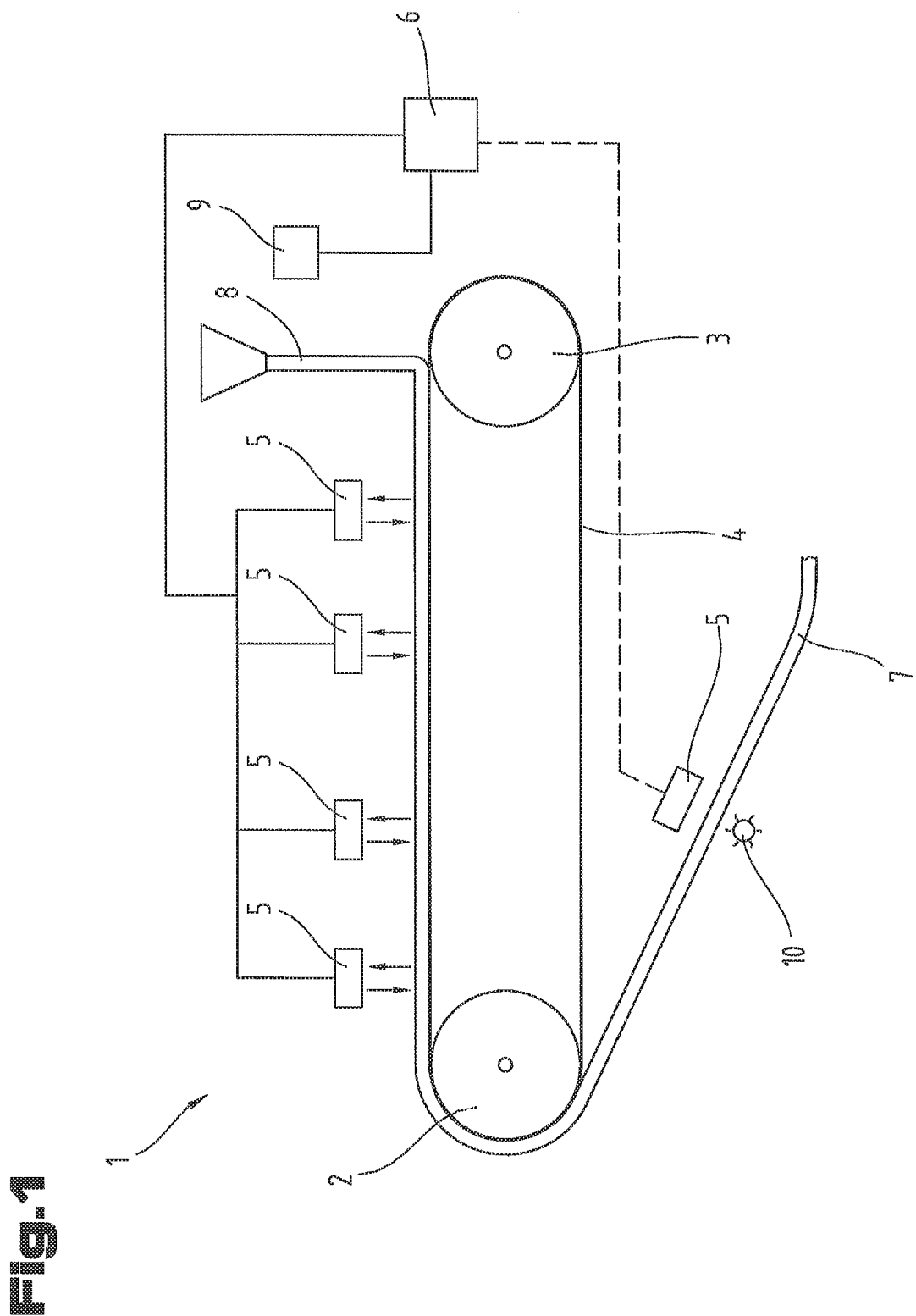

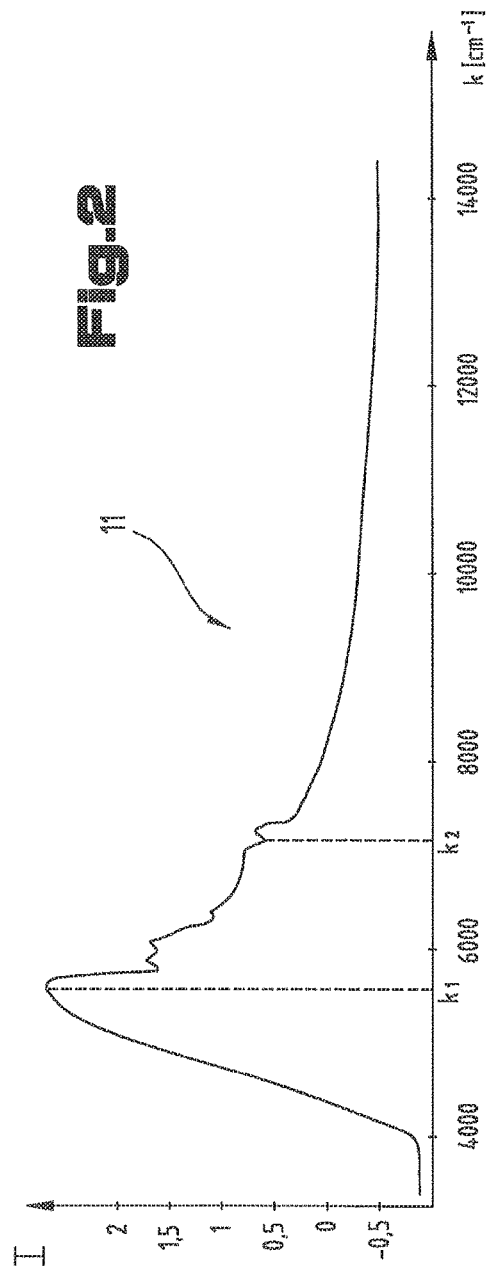

METHOD FOR PRODUCING A FOIL OR A FILM

CROSS REFERENCE TO RELATED APPLICATIONS

This application is the National Stage of PCT/AT2014/050117 filed on May 14, 2014, which claims priority under 35 U.S.C. § 119 of Austrian Application No. A 50326/2013 filed on May 15, 2013, the disclosure of which is incorporated by reference. The international application under PCT article 21(2) was not published in English.

The invention relates to a method of producing a foil or a film as outlined in the introductory part of claim 1.

Methods and devices of the above-mentioned type are known from US2012/0292800A1, JPS61219625 A, U.S. Pat. No. 4,982,500 and W084/01430.

Methods and devices of the type outlined above are used to produce foils or films, for example polyvinyl alcohol foils (PVOH foils), such as used in the medicaments industry for example, or triacetate films (TAC films), which are used to produce LCD screens for example. To this end, an endless belt serving as a processing belt for applying and conveying the film circulates between a driving roller and a pulley roller between which the belt is tensed. Based on the known solutions, a starting material in liquid form is poured onto the belt. The material can then form a homogeneous film on the belt surface, which can then be subjected to other processing steps, such as drying, stretching, cutting, etc. For reasons of easier reading, the term "film" as used below should also be understood as meaning foils and quite generally any type of flat, in particular plate-shaped or strip-shaped, single or multi-layered arrangements of solid substances which may be elastically or non-elastically stretchable or non-stretchable.

In order to obtain a high production rate, the films are removed from the belt in a still moist state. In the case of solvent-based films, the term "moist" refers to the proportion of solvent still contained in the film For example, the proportion of solvent would be zero in the case of a fully dried film. Based on the known solutions, however, it is not possible to determine the proportion of solvent before removing the film from the belt. This is a major problem, however, because the solvent content of solvent-based films is an important parameter in terms of the quality of the film when removed. Based on the known solutions, it is also not possible to measure a change in the process parameters during the production process without interrupting it.

Accordingly, it is an objective of the invention to overcome the problems outlined above.

This objective is achieved by means of a method proposed by the invention of the type outlined above based on the features defined in the characterizing part of claim 1. The invention enables the film-forming process to be monitored without any gaps so that any faults which might occur can be exactly pinpointed.

The solution proposed by the invention offers a simple way of detecting film properties of the material such as the degree to which it is cured and/or the degree to which it has dried and/or its thickness and/or its proportion of solvent as well as other process parameters such as temperature and pressure, etc., exactly during the entire production process by means of a spectrographic analysis of the material without the measurement requiring intervention in the production process and without adversely affecting it.

It has proved to be of particular advantage if an infrared absorption method is used as the spectroscopic method in step b). Infrared spectroscopy has proved to be particularly practical in the context of the invention, although other spectroscopic methods may also be used, such as Raman spectroscopy, for example.

Based on one variant of the invention, at least one actual value for at least one parameter of the material and/or the state variable of the defined area around the belt can be determined from a spectrum detected by means of the spectroscopic method and compared with at least one desired value.

Based on another embodiment of the invention, an actuator can be activated depending on a variance of the actual value from the desired value in order to change at least one of the state variables of the defined area or a conveying speed of the belt.

In the case of a preferred embodiment of the invention, the foil or film is a solvent-based film or a solvent-based foil and evaporating the solvent results in drying and/or curing of the material and in step b), the current solvent content of the material is detected at at least one predefined measurement point.

Based on a preferred variant of the invention, intensity values of individual wavelengths or wavelength ranges in a spectrum can be assigned values for parameters of the material and/or state variables of the defined area around the belt.

The at least one parameter of the material is advantageously the thickness of the material and/or a solvent content of the material.

The at least one state variable of the defined area detected around the belt may be an atmospheric pressure and/or a temperature in the defined area.

To provide a clearer understanding, the invention will be described in more detail below with reference to the appended drawings.

These are highly schematic, simplified diagrams respectively illustrating the following:

FIG. 1 a device as proposed by the invention;

FIG. 2 an infrared spectrum;

FIG. 3 a first table with material parameters and values of state variables which are assigned to different intensity values of a wavelength;

FIG. 4 a second table with material parameters and values of state variables which are assigned to different intensity values of a wavelength.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

As illustrated in FIG. 1, a device 1 proposed by the invention may comprise a belt 4 in the form of an endless belt circulating between a tail pulley 2 and a driving drum 3. However, the invention is not restricted to the use of an endless belt and it would also be possible to use a belt 4 that is not connected at its ends, amongst others, for example, which is reeled off a roller and reeled back on again at one end.

The device 1 comprises one or more spectrometers 5, preferably optical spectrometers, which are connected to a controller 6 of the device 5. At this stage, it should be pointed out that in the context of the invention, it would be possible to use only one spectrometer 5. Where the description refers to spectrometers in the plural, the technical teaching with regard to measuring and evaluating the detected spectra should be understood as meaning that this might involve the use of just one spectrometer 5. The controller 6 may be connected to an actuator 9, by means of which process parameters, such as the temperature in a specific area above the belt 4 or the running speed of the belt 4 etc., can be set. The actuator 9 might be a brake, for example, which acts on the driving drum or a heater, etc.

The device 1 is used to produce a film 7 This film may be a solvent-based film, such as for example so-called TAC films, PVOH films, etc. The solvents used will be, for example in the case of TAC films dichloromethane (methylene chloride) or in the case of PVOH films water.

In accordance with the method proposed by the invention, a material 8 in liquid form is applied to the moving belt 4 in order to produce the film 7. The material 8 can be applied by pouring it, for example by means of curtain coating, extrusion, spraying, etc. The poured material 8 forms a film-forming layer on the belt 4 and is fed on the belt 4 through a process which leads to an at least partial drying and/or curing of the material 8.

By means of a non-invasive spectroscopic method, for which the spectrometer 5 is used, properties of the material 8 and/or thermal state variables of a defined area around the belt 4 can be detected. The defined area of the belt 4 can be set, for example, on the basis of a distance of the respective spectrometer 5 from the surface of the belt 4.

The spectroscopic method is preferably an infrared absorption method. In the context of this invention, it has proved to be particularly practical to use a Fourier transformation infrared spectroscopic method in the near infrared range. Such methods are known by the abbreviated name FT-NIR spectroscopic methods. To this end, the spectrometer 5 used is a Fourier Transform infrared spectrometer (FTIR spectrometer).

The material 8 is illuminated with light wavelengths from the near infrared range and corresponding absorption spectra are measured by means of the spectrometers 5 at different points of the device 1 in a manner known per se. If the measurement is taken above the belt 4, an energizing light source can be positioned above the belt 4 or may also be integrated in the respective spectrometer 5, depending on its design. The emitted light passes through the material 8 and a transmitted part is reflected on the surface of the belt 4, which is preferably provided in the form of a metal belt with a closed surface. Some of the light is absorbed by the material 8. The directions of the incident and reflected light are indicated by arrows in FIG. 1. Using the incident light from the respective spectrometer 5 which is reflected by the surface of the belt 4 and passes through the material 8 in the direction of the corresponding spectrometer 5, the spectrum 11 illustrated in FIG. 2 in the form of an NIR absorption spectrum is then obtained. If the measurement is not taken above the (reflecting) belt surface but in a region where the material 8 is already present in the form of a removed film 7, a light source 10 must be disposed opposite the spectrometer 5. The film 7 is then fed between the light source 10 and the spectrometer 5.

FIG. 2 plots the intensity over the wave number k. In the spectrum 11, there are characteristic wave numbers $k_1$, $k_2$, which enable information about a specific material parameter to be obtained, such as the solvent content of the material, for example. The characteristic wave numbers $k_1$, $k_2$ lie in ranges in which a solvent used has a high absorption, for example.

As may be seen from the tables of FIGS. 3 and 4, different intensity values $I_1$, $I_{11}$, $I_{12}$, $I_{1i}$, $I_2$, $I_{21}$, $I_{22}$, $I_{2i}$ of individual characteristic wavelengths or wavelength ranges in the spectrum 11 can be assigned to values for parameters of the material and/or state variables of the defined area around the belt 4.

Individual parameters of the material or, for example, also the process temperature $T_1$, $T_{11}$, $T_{12}$, $T_{1i}$, $T_2$, $T_{21}$, $T_{22}$, $T_{2i}$ at a specific point of the process can be assigned by directly assigning the measured values for a specific wave number $k_1$, $k_{12}$, $k_{1i}$, $k_2$, $k_{22}$, $k_{2i}$ to a concrete value of the parameter or temperature. For example, the current solvent content $L_1$, $L_{11}$, $L_{12}$, $L_{1i}$, $L_2$, $L_{21}$, $L_{22}$, $L_2$ of the material 8 can be measured by weighing the film and at the same time the intensities $I_1$, $I_{11}$, $I_{12}$, $I_{1i}$, $I_2$, $I_{21}$, $I_{22}$, $I_{2i}$ of the wave numbers $k_1$ and $k_2$ or the maximum intensities $I_1$, $I_{11}$, $I_{12}$, $I_{1i}$, $I_2$, $I_{21}$, $I_{22}$, $I_{2i}$, are determined in a range of pre-definable variables around these wave numbers. At the same time, the process temperature in a fixed area around the belt 4 can be measured. These measurements can be taken for different solvent contents to enable intensity values $I_1$, $I_{11}$, $I_{12}$, $I_{1i}$, $I_2$, $I_{21}$, $I_{22}$, $I_{2i}$ to be assigned to solvent contents and temperatures $T_1$, $T_{11}$, $T_{12}$, $T_{1i}$, $T_2$, $T_{21}$, $T_{22}$, $T_{2i}$ as may be seen from the tables of FIG. 3 and FIG. 4. At this stage, it should also be pointed out that a solvent content and the process temperature are correlated to one another to a very high degree, so that it is also possible to derive the corresponding temperature from the solvent content. In principle, other parameters can also be assigned to the intensity values $I_1$, $I_{11}$, $I_{12}$, $I_{1i}$, $I_2$, $I_{21}$, $I_{22}$, $I_{2i}$, in which case using the approach outlined above, the intensity values can also be assigned to material thicknesses which are likewise strongly correlated to the solvent content, or a pressure in the area of the belt 4 as well as other process parameters.

The approach to obtaining information from the spectrum 11 described above constitutes a simple method of directly obtaining the values of corresponding process parameters from the spectrum 11. Naturally, information about the corresponding values of process parameters can also be obtained from the spectrum 11 using quantitative methods based on signal processing.

For example, using the spectrum 11, an actual value for a parameter of the material 8 and/or the state variable of the defined area around the belt 4 can be determined and compared with a desired value. The evaluation of the spectrum 11 and comparison with the desired values are run by the controller 6, for example a microprocessor or signal processor programmed accordingly. The desired values can be stored in a memory connected to the controller 6, although this is not illustrated. Depending on a variance of the actual value from the desired value, the controller 6 can be operated so as to activate the actuator 9 in order to change at least one of the state variables of the defined area or a conveying speed of the belt 4. This being the case, the controller 6 can change the temperature or adjust the speed of the belt 4 at a specific point of the process via the actuator 9, for example, in order to increase or reduce the dwell time of the material 8 in the process.

If the film 7 is a solvent-based film, evaporating the solvent during the process dries and/or cures the material 8.

In this case, the current solvent content $L_1$, $L_{11}$, $L_{12}$, $L_{1i}$, $L_2$, $L_{21}$, $L_{22}$, $L_{2i}$ at a measurement point of the material 8 may be detected as the actual value and compared with a desired value.

By using several spectrometers 5, the distance between the point of applying the material 8 and peeling off the film 7 can be divided into sections and a spectrometer 5 assigned to each section. This being the case, a separate set of desired values can be assigned to each spectrometer 5. Any variance which occurs between actual values and desired values can then be locally identified in an exact manner as a result, enabling a specific type of intervention in the process.

For the sake of good order, it should be pointed out that to provide a clearer understanding of the structure of the device proposed by the invention, it and its constituent parts are illustrated to a certain extent out of scale and/or on a larger scale and/or on a smaller scale.

The embodiments illustrated as examples represent possible variants of the method proposed by the invention, and it should be pointed out at this stage that the invention is not specifically limited to the variants specifically illustrated. All the individual variants based on the wording of the independent claims fall within the protective scope of the invention.

LIST OF REFERENCE NUMBERS

1 Device
2 Tail pulley
3 Driving drum
4 Belt
5 Spectroscope
6 Controller
7 Film
8 Material
9 Actuator
10 Light source
11 Spectrum
$I_1$, $I_{11}$, $I_{12}$, $I_{1i}$, Intensity values
$I_2$, $I_{21}$, $I_{22}$, $I_{2i}$ Intensity values
$k_1$, $k_{12}$, $k_{1i}$, Wave number
$k_2$, $k_{22}$, $k_{2i}$ Wave number
$L_1$, $L_{11}$, $L_{12}$, $L_{1i}$ Solvent content
$L_2$, $L_{21}$, $L_{22}$, $L_{2i}$ Solvent content
$T_1$, $T_{11}$, $T_{12}$, $T_{1i}$ Temperature
$T_2$, $T_{21}$, $T_{22}$, $T_{2i}$ Temperature

The invention claimed is:

1. Method for producing a foil or a film, comprising the following steps
   a) applying at least one material for producing the foil or film to a moving belt,
   b) at least partially curing and/or partially drying the material
   and
   during step b) properties of the material are recorded via at least one non-invasive spectroscopic method, wherein the material is poured onto the belt at a first point and the at least partially cured and/or dried material is removed from the belt at a second point, and a distance covered between the first and second point is divided into sections of the same or a different size, and parameters of the material are recorded by means of the non-invasive spectroscopic method in each of the sections at pre-definable intervals, wherein a film-forming process between the first point and the second point is monitored without any gaps in a direction of movement of the belt and any malfunctions are exactly pinpointed.

2. Method according to claim 1, wherein in step b) an infrared absorption method is used as the spectroscopic method.

3. Method according to claim 1, wherein from a spectrum recorded via the spectroscopic method, at least one actual value for at least one parameter of the material is determined and compared with at least one desired value.

4. Method according to claim 3, wherein depending on a variance of the actual value from the desired value, an actuator is activated in order to change a conveying speed of the belt.

5. Method according to claim 1, wherein the foil or film is a solvent-based film or a solvent-based foil and evaporation of a solvent results in drying and/or curing of the material and in step b), the current solvent content of the material is recorded at at least one predefined measurement point.

6. Method according to claim 1, wherein intensity values of individual wavelengths or wavelength ranges in a spectrum are assigned to values for parameters of the material.

7. Method according to claim 3, wherein the at least one parameter of the material is a thickness of the material.

* * * * *